United States Patent
Moszner et al.

(10) Patent No.: US 6,713,555 B2
(45) Date of Patent: Mar. 30, 2004

(54) HYDROLYZABLE AND POLYMERIZABLE SILANES BASED ON METHYLENE DITHIEPANE

(75) Inventors: Norbert Moszner, Eschen (LI); Sabine Stein, Nenzing (AT); Thomas Völkel, Oberreitnau (DE); Volker Rheinberger, Vaduz (LI)

(73) Assignee: Ivoclar AG, Schaan (LI)

( * ) Notice: Subject to any disclaimer, the term of this patent is extended or adjusted under 35 U.S.C. 154(b) by 0 days.

(21) Appl. No.: 10/260,069

(22) Filed: Sep. 27, 2002

(65) Prior Publication Data

US 2003/0060535 A1 Mar. 27, 2003

Related U.S. Application Data

(62) Division of application No. 09/657,343, filed on Sep. 7, 2000.

(30) Foreign Application Priority Data

Sep. 8, 1999 (DE) .......................... 199 43 712

(51) Int. Cl.⁷ .................. C08L 83/08; C08G 77/28; A61K 6/093
(52) U.S. Cl. ................ 524/588; 523/115; 523/116; 523/118; 523/120; 526/286; 528/25; 528/30; 528/32
(58) Field of Search .............. 524/588; 528/25, 528/30, 32; 523/115, 116, 118, 120; 526/286; 549/10, 11

(56) References Cited

U.S. PATENT DOCUMENTS 5,397,824 A   3/1995   McVie et al.

6,043,361 A * 3/2000 Evans et al. .................. 544/1

FOREIGN PATENT DOCUMENTS

WO   WO 96/19471   6/1996

\* cited by examiner

*Primary Examiner*—Tae H. Yoon
(74) *Attorney, Agent, or Firm*—Nixon Peabody LLP

(57) ABSTRACT

Methylene dithiepane silanes according to Formula I

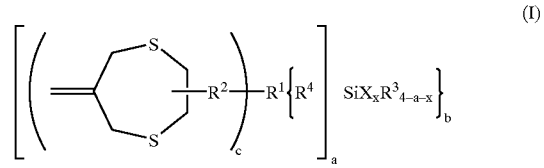

in which $R^1$ is a saturated or unsaturated aliphatic or alicyclic hydrocarbon radical with 1 to 10 carbon atoms, which can be interrupted by one or more oxygen and/or sulphur atoms and can contain one or more ester, carbonyl, amide and/or urethane groups, or is an aromatic or heteroaromatic hydrocarbon radical with 6 to 18 carbon atoms, the hydrocarbon radicals being able to be substituted or unsubstituted; $R^2$ has one of the meanings given for $R^1$ or is absent; $R^3$ has one of the meanings given for $R^1$ or is absent; $R^4$ is equal to $-(CHR^6)_n-$, $-Y-CO-NH-(CHR^6)_n-$, $-Y-CO-NH-R^5-$, $-(CHR^6)_n-S-R^5-$, $-S-R^5-$, $-CO-O-R^5-$ or is absent, with n being equal to 1 to 4, $R^6$ is hydrogen, $C_1$ to $C_{10}$ alkyl or $C_6$ to $C_{10}$ aryl, $R^5$ has one of the meanings given for $R^1$ and Y stands for an O or S atom or is absent; with $R^5$ and $R^6$ being able to be substituted or unsubstituted; X is a hydrolyzable group; a, b, c and x each independently of each other being 1, 2 or 3; and the sum of a+x=2 to 4. The silanes are particularly suitable for the preparation of dental materials.

21 Claims, No Drawings

HYDROLYZABLE AND POLYMERIZABLE SILANES BASED ON METHYLENE DITHIEPANE

This application is a division of U.S. patent application Ser. No. 09/657,343, filed Sep. 7, 2000 which is herein incorporated by reference in its entirety.

The invention relates to silanes based on methylene dithiepane which are suitable in particular for the preparation of dental materials.

Hydrolyzable silanes which contain polymerizable organic radicals are used in the preparation of coatings, particulate fillers, adhesive materials and monolithic moulded bodies as well as in the surface modification of strengthening materials. The silanes are hydrolytically condensed and polymerized, i.e. cured, thermally, photochemically or by redox initiation, alone, mixed with other silanes or in the presence of other metal alkoxides.

It is above all organically modified silanes with polymerizable organic groups such as vinyl, (meth)acryl, allyl or styryl groups that are of particular interest in connection with the preparation of organic-inorganic composite materials as they allow the simultaneous or consecutive construction of both an inorganic and an organic network and thus of composite materials with made-to-measure properties (cf. H. Schmidt, Mat. Res. Soc. Symp. Proc. Vol. 32 (1984), 327–335; H. Schmidt, H. Wolter, J. Non-Cryst. Solids 121 (1990), 428–435). The polymerizable silanes are usually first hydrolytically condensed in solution. After the addition of a thermal initiator or photoinitiator and removal of the solvent, nanoparticulate resins form which are polymerized after shaping and thus cured.

A significant disadvantage of these materials is that the development of the organic network taking place during polymerization is mostly accompanied by a considerable contraction in volume which can lead to the deformation of the moulded bodies, to a reduction in the substrate adhesion, to a separation of the layers, to the development of voids or to the development of material stresses. There is a reduced contraction in volume in the case of silanes which carry ring-opening groups. In this regard, EP 0 358 011 A2 describes scratch-resistant materials inter alia on the basis of 3-glycidyl oxypropyl silanes and EP 0 486 469 A1 organic-inorganic hybrid polymers of 3-glycidyl oxypropyl silanes.

Furthermore, dental materials based on polymerizable silanes are known. DE 36 10 804 A1 discloses dental resin compounds which contain siloxane polymers, monomers which are co-polymerizable with the siloxane polymers and a polymerization catalyst. The dental resin compounds are said to have an improved compression resistance, abrasion resistance and flexural strength after polymerization.

DE 34 07 087 A1 and WO 92/16183 relate to the use of compositions based on organically modified silicic acid polycondensates to coat teeth and dental prostheses. The cured coats are said to be resistant vis-à-vis the build-up of plaque.

Dental resin compounds based on polymerizable polysiloxanes are known from DE 41 33 494, which are obtained by hydrolytic condensation of silanes with 1,4,6-trioxaspiro-[4,4]-nonane radicals. Silanes with orthoester groups are difficult to access and not very storage-stable. In addition, silanes with epoxide or spiroorthoester groups can only be cationically polymerized, which makes it necessary to exclude moisture. In addition, the polymerization of the epoxide silanes proceeds sufficiently quickly only at increased temperatures.

DE 196 19 046 discloses low-shrinkage polymerizable compositions based on mercapto- or norbornene silanes and a reaction partner for en-thiole polymerization.

DE 197 14 320 A1 relates to dental materials based on vinylcyclopropane silanes and DE 197 14 324 A1 to dental materials based on oxetane silanes.

Furthermore, methylene dithiepane group-containing monomers, such as e.g. dimethyldi-[2-(6-methylene-1,4-diethiepane)methoxy]silane (DMTEPS), are known from WO 96/19471, which can be radically polymerized accompanied by ring-opening. DMTEPS contains no hydrolyzable groups which would allow a hydrolytic condensation yielding polysiloxanes. Rather, the dithiepane radicals are split off during the hydrolysis.

The object of the invention is to prepare silanes based on methylene dithiepane, which can be covalently incorporated into organic-inorganic composite materials, can be polymerized rapidly at room temperature and display only a low shrinkage during polymerization.

The object is achieved by silanes according to formula (I) which contain at least one methylene dithiepane group:

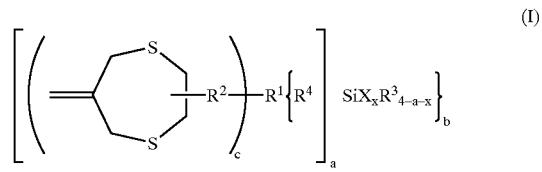

(I)

$R^1$ = a saturated or unsaturated aliphatic or alicyclic hydrocarbon radical with 1 to 10 carbon atoms which can be interrupted by one or more oxygen and/or sulphur atoms and can contain one or more ester, carbonyl, amide and/or urethane groups, or an aromatic or heteroaromatic hydrocarbon radical with 6 to 18 carbon atoms and optionally one or more, preferably one or two heteroatoms, preferably S, O and/or N atoms;

$R^2$ = one of the meanings given for $R^1$ or is absent;

$R^3$ = one of the meanings given for $R^1$ or is absent;

$R^4$ = —$(CHR^6)_n$—, —Y—CO—NH—$(CHR^6)_n$—, —Y—CO—NH—$R^5$—, —$(CHR^6)_n$—S—$R^5$—, —S—$R^5$—, —CO—O—$R^5$— or is absent, where n=1 to 4, $R^6$=hydrogen, $C_1$ to $C_{10}$ alkyl or $C_6$ to $C_{10}$ aryl, $R^5$ has one of the meanings given for $R^1$ and Y stands for an O— or S— atom or is absent;

X = a hydrolyzable group;

a, b, c and x are 1, 2 or 3 each independently of each other; with the sum of a+x=2 to 4.

Preferably, b is equal to 1 when a is greater than 1 and a is equal to 1 when b is greater than 1.

The hydrocarbon radicals also include alkylaryl radicals, such as e.g. $CH_3$—Ph—, aryl alkylene groups, such as e.g. >CH—Ph, and arylene alkylene radicals, such as e.g. —$CH_2$—Ph— or >CH—Ph—CH<, hydrocarbon radicals with $C_7$ to $C_{18}$ C-atoms being preferred.

In the overall description as well as the claims, alkyl is understood to mean linear, branched or cyclic radicals which preferably contain 1 to 12 carbon atoms, more preferably 1 to 8 carbon atoms and most preferably 1 to 4 carbon atoms. Special examples of possible alkyl groups are methyl, ethyl, n-propyl, iso-propyl, sec.-butyl, tert.-butyl, n-pentyl, cyclohexyl, 2-ethylhexyl and octadecyl.

Aryl is understood to mean radicals, groups or substituents which preferably have 6 to 10 carbon atoms and can be substituted as given above. Preferred aryl groups are phenyl, biphenyl and naphthyl.

The alkoxy and acyloxy groups are derived from the above-named alkyl and aryl radicals. Special examples are methoxy, ethoxy, n-propyl, isopropyl, tert.-butyloxy, acetyloxy, acetyl, benzyl, 2-phenylethyl and tolyl.

The above-named radicals and groups can be unsubstituted or carry one or more substituents, in particular alkyl, aryl, halogen, preferably chlorine, hydroxy, alkoxy, hydroxyalkyl, carboxy, —$SO_3H$, —$PO_3H_2$ and/or —$PO_4H_2$.

The ester, carbonyl, amide and urethane groups which are possibly present in the radicals are defined by the following formulae: —CO—O—, —O—CO—, —CO—, —CO—NH—, —NH—CO—, —O—CO—NH—, —NH—CO—O—. The groups can be integrated into the radicals or be terminally bonded thereto.

Preferred definitions, which can be chosen independently of each other, for the individual variables are:

$R^1$ = a saturated or unsaturated aliphatic or alicyclic hydrocarbon radical with 1 to 8 carbon atoms which can be interrupted by oxygen or sulphur atoms, ester, carbonyl, amide and/or urethane groups, or an aromatic hydrocarbon radical with 6 to 10 carbon atoms; in particular a saturated or unsaturated aliphatic or alicyclic hydrocarbon radical with 1 to 6 carbon atoms or an aromatic hydrocarbon radical with 6 to 10 carbon atoms;

$R^2$ = a saturated or unsaturated aliphatic or alicyclic hydrocarbon radical with 1 to 8 carbon atoms which can be interrupted by oxygen or sulphur atoms, ester, carbonyl, amide and/or urethane groups, or an aromatic hydrocarbon radical with 6 to 10 carbon atoms; in particular a saturated or unsaturated aliphatic hydrocarbon radical with 1 to 4 carbon atoms which can contain an oxygen atom or an ester group, or is absent;

$R^3$ = a saturated or unsaturated aliphatic or alicyclic hydrocarbon radical with 1 to 8 carbon atoms which can be interrupted by oxygen or sulphur atoms, ester, carbonyl, amide and/or urethane groups, or an aromatic hydrocarbon radical with 6 to 10 carbon atoms; in particular a methyl, ethyl and/or phenyl group, or is absent;

$R^4$ = —$(CHR^6)_n$—, —Y—CO—NH—$(CHR^6)_n$—, —Y—CO—NH—$R^5$—, —S—$R^5$—, —CO—O—$R^5$— or is absent, with n=1 to 3, $R^6$=hydrogen or $C_1$ to $C_4$ alkyl, $R^5$ has one of the meanings given for $R^1$, in particular one of the preferred meanings, and Y stands for an O— or S— atom or is absent, in particular —$(CH_2)_n$— or —Y—CO—NH—$(CH_2)_n$—, with n=1 to 3, and Y stands for an O— atom or is absent;

X=halogen, hydroxy, $C_1$ to $C_3$ alkoxy or $C_1$ to $C_3$ acyloxy; in particular methoxy, ethoxy or chlorine;

a=1;

b=1 or 2;

c=1 or 2; and/or x=2 or 3.

The 1,4-dithiepane ring of the silane is preferably substituted in position 2 or 3.

Preferred versions of the methylene dithiepane silanes of Formula (I) according to the invention are compounds according to the following formulae II to V.

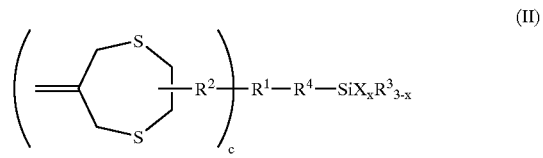

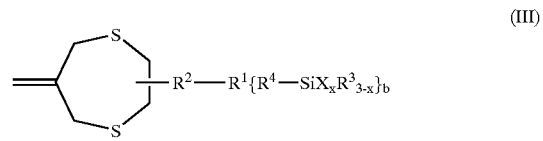

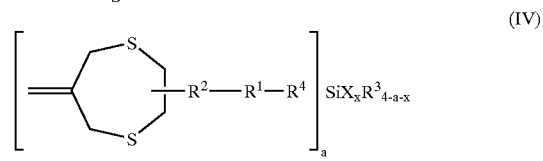

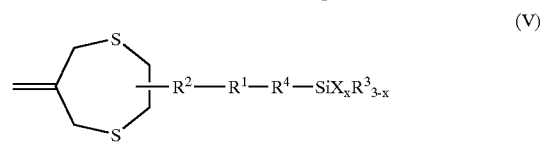

Specific examples of particularly preferred silanes according to Formula (I) are:

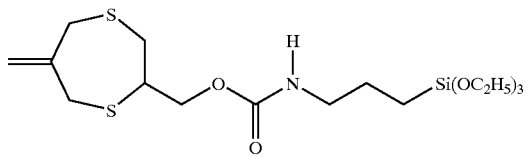

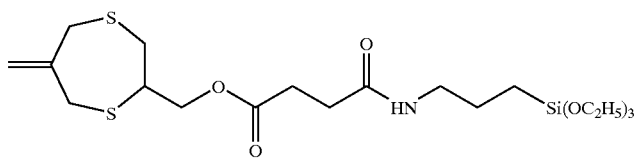

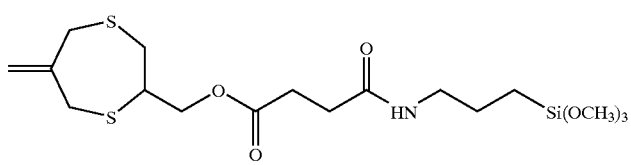

-continued

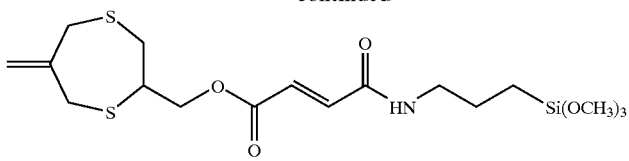

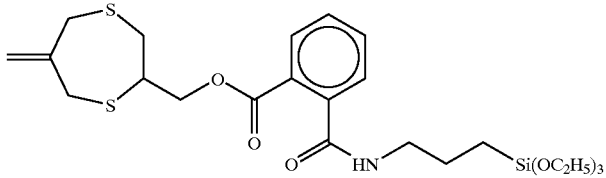

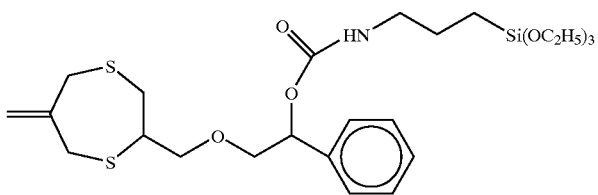

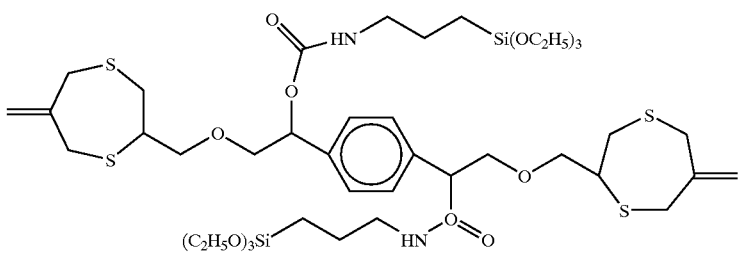

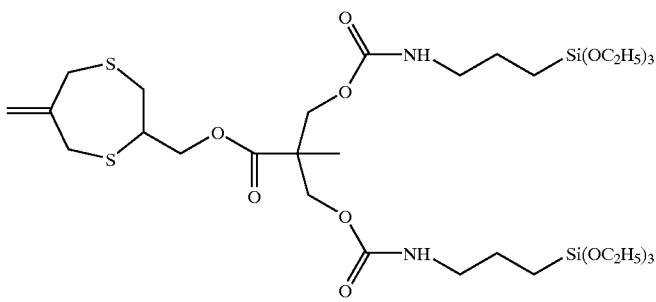

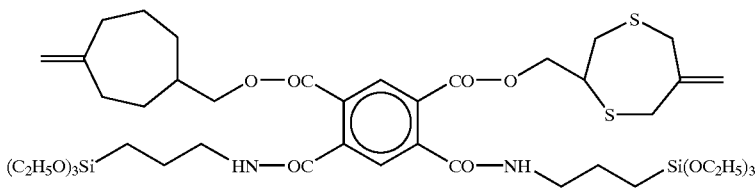

The silanes of formula (I) are accessible via addition and condensation reactions known per se, the number of hydrolyzable groups, polymerizable groups and further functional groups being able to be varied by the suitable choice of educts.

Functionalized 2-methylene-dithiepane precursors suitable for silane synthesis are for example accessible by reaction of mono- or multicarboxylic acid anhydrides (A) or mono- or multiepoxides (B) with hydroxymethyl-6-methylene-1,4-diethiepane, the synthesis of which is described in WO 96/19471. Subsequently, the carboxyl groups (A) or hydroxyl groups (B) formed during this reaction are reacted e.g. with 3-isocyanatopropyl triethyoxy silane.

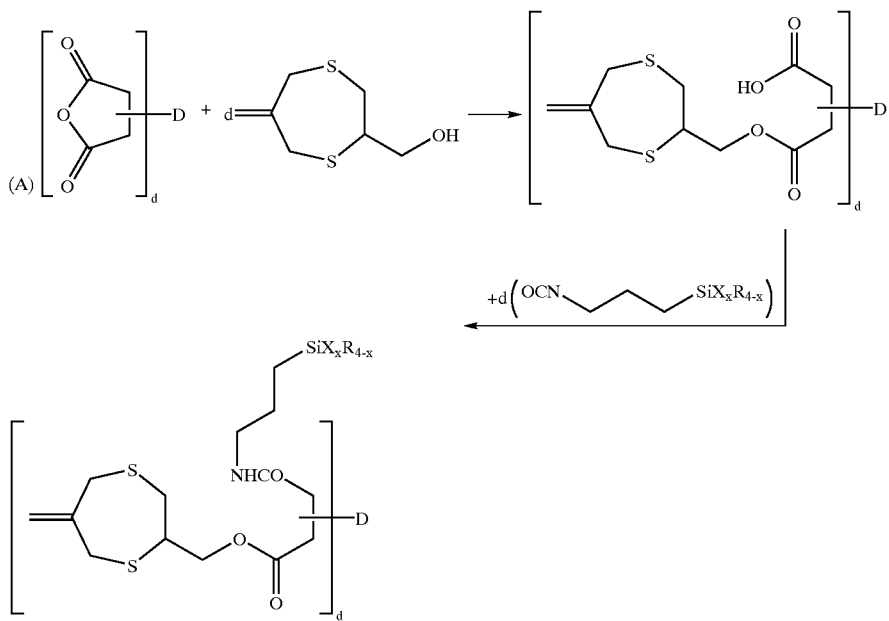

The methylene dithiepane silanes according to the invention are radically polymerizable by ring-opening polymerization via the methylene dithiepane group and hydrolytically condensable via the radicals X. The ring-opening polymerization of the dithiepane rings leads to the development of an organic network whilst the hydrolyzable groups produce an inorganic polysiloxane network through polycondensation. A particular advantage of the silanes according to the invention can be seen in the fact that they can be radically polymerized at high speed at room temperature, but at the same time are very stable. Moreover, the products obtained after hydrolytic polycondensation and radical polymerization are not sensitive to moisture.

A further advantage of the silanes according to the invention is their unexpectedly high refractive index. In general, this lies above 1.50 and preferably above 1.52 and quite particularly preferably in the range of 1.53 to 1.55 (measured for the D line of sodium light at 25° C.), i.e. in the range of the refractive index of usual dental fillers. Thus, the silanes according to the invention allow an exact matching of the refractive indices of silane and filler and thus the preparation of dental materials with high transparency.

The silanes according to the invention can be used as such, in hydrolytically condensed form or in partially polymerized form. In general, the silanes are firstly hydrolytically condensed and the polysiloxanes obtained in the process are subsequently cured by ring-opening polymerization.

The silanes (I) can be processed either alone or together with other hydrolytically condensable compounds of silicon, aluminium, zirconium, titanium, boron, tin and/or vanadium to produce the polysiloxanes. These additional compounds can be used either as such or in precondensed form.

Preferred further hydrolytically condensable compounds of silicon are silanes of the general formula (VI)

$R^7{}_k(Z'R^8)_m SiX'_{4-(k+m)}$  Formula (VI)

in which
$R^7$ stands for a $C_1$ to $C_8$ alkyl, $C_2$ to $C_{12}$ alkenyl or $C_6$ to $C_{14}$ aryl group;
$R^8$ stands for a $C_1$ to $C_8$ alkylene, $C_2$ to $C_{12}$ alkenylene or $C_6$ to $C_{14}$ arylene group;
X' stands for a hydrogen or halogen atom or a $C_1$ to $C_8$ alkoxy group;
Z' stands for a glycidyl, acryl, methacryl, vinyl, allyl or vinyl ether group;
k is equal to 0, 1, 2 or 3;
m is equal to 0, 1, 2 or 3; and
k+m is equal to 0, 1, 2 or 3.

Preferred definitions, which can be chosen independently of each other, for the individual variables are:
$R^7$=a $C_1$ to $C_3$ alkyl, $C_2$ to $C_5$ alkenyl or a phenyl group;
$R^8$=a $C_1$ to $C_5$ alkylene, $C_2$ to $C_5$ alkenylene or a phenylene group;
X'=a halogen atom, a methoxy or ethoxy group;
Z'=an acryl or methacryl group;
k=0 and 1;
m=0 and 1;
k+m=0, 1 or 2.

Such silanes are described for example in DE 34 07 087 A1. Particularly preferred silanes of formula (VI) are:
$CH_3$—$SiCl_3$, $CH_3$—$Si(OC_2H_5)_3$, $C_2H_5$—$SiCl_3$, $C_2H_5$—$Si(OC_2H_5)_3$, $CH_2$=$CH$—$Si(OC_2H_5)_3$, $CH_2$=$CH$—$Si(OCH_3)_3$, $CH_2$=$CH$—$Si(OC_2H_4OCH_3)_3$, $(CH_3)_2SiCl_2$, $(CH_3)_2Si(OC_2H_5)_2$, $(C_2H_5)_3Si$—$Cl$, $(C_2H_5)_2Si(OC_2H_5)_2$, $(CH_3)_3Si$—$Cl$, $(CH_3O)_3Si$—$C_3H_6NH_2$, $(CH_3O)_3Si$—$C_3H_6SH$, $(CH_3O)_3Si$—$C_3H_6NH_2$,

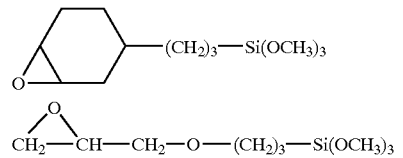

Silanes of the general formula (VI) or precondensed products derived from them are used preferably in a quantity of 0 to 90 mol-%, more preferably 1 to 60 mol-% and most preferably 1 to 40 mol-% relative to the total mass of silanes of formulae (I) and (VI) or precondensed products derived from them.

Preferred zirconium and titanium compounds are those according to formula (VII)

 Formula (VII)

in which

Me stands for Zr or Ti;

$R^9$ stands for a hydrogen atom, a substituted or unsubstituted $C_1$ to $C_{12}$ alkyl, $C_1$ to $C_{15}$ alkylaryl or $C_6$ to $C_{14}$ aryl group;

X" stands for a halogen atom, a hydroxyl or $C_1$ to $C_8$ alkoxy group;

Y is equal to 1 to 4;

Z is equal to 0 to 3.

Preferred definitions, which can be chosen independently of each other, for the individual variables are:

$R^9$=a $C_1$ to $C_5$ alkyl or a phenyl group;

X"=a halogen atom, a methoxy, ethoxy or propoxy group;

Y=4;

Z=0 or 1, in particular 0.

Particularly preferred zirconium and titanium compounds are $ZrCl_4$, $Zr(OC_2H_5)_4$, $Zr(OC_3H_7)_4$, $Zr(OC_4H_9)_4$, $ZrOCl_2$, $TiCl_4$, $Ti(OC_2H_5)_4$, $Ti(OC_3H_7)_4$ and $Ti(OC_4H_9)_4$.

The zirconium and titanium compounds of general formula (VII) or precondensed products derived from them are preferably used in a quantity of 0 to 70 mol-%, more preferably 0 to 50 mol-% or 0 to 30 mol-% and most preferably 0 to 20 mol-% relative to the total mass of compounds of formulae (I) and (VII) or precondensed products derived from them.

Preferred aluminium compounds are those according to formula (VIII)

 Formula (VIII)

in which $R^{10}$ stands for a halogen atom, a hydroxyl or $C_1$ to $C_8$ alkoxy group, preferably for a halogen atom or a $C_1$ to $C_5$ alkoxy group.

Particularly preferred aluminium compounds are $Al(OCH_3)_3$, $Al(OC_2H_5)_3$, $Al(OC_3H_7)_3$, $Al(OC_4H_9)_3$ and $AlCl_3$.

The aluminium compounds of general formula (VIII) or precondensed products derived from them are preferably used in a quantity of 0 to 70 mol-%, more preferably 0 to 30 mol-% and most preferably 0 to 20 mol-% relative to the total mass of compounds of formulae (I) and (VIII) or precondensed products derived from them.

In addition, complexed compounds of zirconium, titanium and aluminium can be used, with acids and β-dicarbonyl compounds being preferred as complexing agents. Preferred acids are acrylic and methacrylic acids or other methacrylate carboxylic acids such as e.g. 2-methacryloyl oxyethyl hydrogen succinate or the 1:1 adducts of glycerol dimethacrylate and carboxylic acid anhydrides such as e.g. succinic or phthalic anhydride. Preferred β-carbonyl compounds are acetylacetone, acetoacetic acid ethyl ester and in particular 2-acetoacetoxyethyl methacrylate. These complexing agents are preferably reacted with alkoxy derivatives of zirconium, titanium or aluminium in the molar ratio of 1:1.

In addition, boron trihalides, tin tetrahalides, tin tetraalkoxides and/or vanadyl compounds are suitable for co-condensation with the silanes according to formula (I).

When using additional hydrolytically condensable compounds, the proportion of silanes according to formula (I) in the polysiloxanes is preferably 10 to 100 mol-%, more preferably 40 to 100 mol-%, each relative to the monomeric starting compounds. The proportion of silanes (I) and (VI) together is preferably at least 20 mol-%, more preferably at least 80 mol-%, also relative to the monomeric starting compounds.

The preparation of the polysiloxanes is carried out by hydrolytic condensation of the compounds listed above. In the case of silanes of the general formulae (I) and (VI), the hydrolyzable groups X are first split off, silanols, silane diols and silane triols being obtained which condense accompanied by splitting-off of water to give polysiloxanes with an inorganic network of Si—O—Si units.

In general the hydrolytic condensation of the silanes is carried out by reacting the silicon compound to be hydrolyzed either directly or dissolved in a suitable solvent at a temperature of 0 to 100° C., preferably 20 to 80° C. and more preferably between 20 and 50° C., at least with the quantity of water stochiometrically required for complete hydrolysis, and stirring the resulting mixture for one or more hours. Suitable in particular as solvents are aliphatic alcohols, such as for example ethanol or isopropanol, dialkyl ketones, such as acetone or methyl isobutyl ketone, ethers, such as for example diethyl ether or tetrahydrofuran (THF), esters, such as for example ethyl or butyl acetate and mixtures thereof.

The hydrolysis and condensation of the starting mixture is preferably carried out in the presence of a condensation catalyst, compounds which split off protons or hydroxyl ions, such as organic or inorganic acids or bases, as well as compounds releasing fluoride ions, such as ammonium fluoride or sodium fluoride being preferred. Particularly preferred are volatile acids or bases, in particular hydrochloric acid or ammonium hydroxide. It has proved worthwhile to adopt the procedures of the sol-gel technique during hydrolysis and condensation, as described for example in C. J. Brinker et al., "Sol-Gel-Science", Academic Press, Boston, 1990.

If the hydrolytic condensation is carried out in the presence of zirconium, titanium or aluminium compounds, the addition of water is carried out preferably in stages, the temperature preferably being kept in the range of approximately 0 to 30° C. It is often advantageous for water to be added in the form of aqueous solvents, such as for example aqueous ethanol, or produced in situ, for example by chemical reactions such as esterifications.

The polysiloxanes obtained can be used directly or after partial or complete removal of the solvent. It is often advantageous to replace the solvent used for the hydrolytic condensation with another solvent. The silanes (I) and in particular the polysiloxanes have only a low volatility due to their high molecular weight and can therefore largely be safely processed. With regard to the mechanical properties of the polysiloxanes, it is advantageous to carry out the hydrolytic condensation up to a degree of condensation of 65 to 95%, the degree of condensation being measured by $^{29}$Si-NMR.

The complete curing of the polysiloxanes is carried out by the addition of suitable initiators and optionally further polymerizable components by thermal, photochemical or redox-induced polymerization. If various polymerizable groups are present, e.g. (meth)acrylic and epoxide groups, several curing mechanisms, e.g. radical and cationic polymerization, can be used simultaneously or in consecutive stages.

To initiate the radical polymerization, thermal and/or photoinitiators are preferably used.

Preferred initiators for the thermal curing are peroxides, such as for example dibenzoyl peroxide, dilauryl peroxide, tert.-butyl peroctoate and tert.-butyl perbenzoate as well as azobisisobutyroethyl ester, benzopinacol and 2,2-dimethyl benzopinacol.

Preferred photoinitiators are benzophenone and benzoin as well as their derivatives, α-diketones and their derivatives, such as for example 9,10-phenanthrenequinone, diacetyl and 4,4-dichlorobenzil. Particularly preferred photoinitiators are camphorquinone and 2,2-methoxy-2-phenyl-acetophenone and in particular combinations of α-diketones with amines as reduction agents, such as for example N-cyanoethyl-N-methylaniline, 4-(N,N-dimethylamino)-benzoic acid ester, N,N-dimethyl aminoethyl methacrylate, N,N-dimethyl-sym.-xylidine or triethanolamine. In addition, acyl phosphines, such as for example 2,4,6-trimethylbenzoyldiphenyl or bis-(2,6-dichlorobenzoyl)-4-N-propylphenyl phosphine oxide are suitable as photoinitiators.

Diaryliodonium or triarylsulphonium salts, such as for example triphenylsulphonium hexafluorophosphate and hexafluoroantimonate, are particularly suitable for the dual curing of radically and cationically polymerizable systems.

Redox-initiator combinations, such as for example combinations of benzoyl or lauryl peroxide with N,N-dimethyl-sym.-xylidine or N,N-dimethyl-p-toluidine are used as initiators for a polymerization at room temperature.

The polymerization of polysiloxanes with two or more methylene dithiepane radicals results in three-dimensional, organic networks, and the mechanical properties, such as for example strength and flexibility as well as the physical-chemical properties of the cured materials, such as for example the adhesive power, absorption of water and refractive index can be varied via the distance between the Si— atoms and the polymerizable methylene dithiepane radicals, i.e. over the length of the spacer group —$R^2$—$R^1$—$R^4$— as well as via the presence of further functional groups, and optimally adapted to the requirements of the respective application case. The use of aliphatic groups as spacers results in relatively flexible products and the use of aromatic groups relatively rigid products.

The cross-linking density of the cured materials can be set through the number of polymerizable methylene dithiepane groups, which allows a further influencing of the properties and possible uses of the polysiloxanes.

If, in addition, the monomeric silanes contain ionically cross-linkable groups, such as for example epoxide or oxethane groups, a further increase in the cross-linking density can be achieved through their simultaneous or subsequent ionic polymerization.

The polysiloxanes can be used mixed with suitable ionically and/or radically polymerizable mono or multifunctional monomers. Preferred monomers are mono(meth)acrylates such as methyl, ethyl, butyl, benzyl, furfuryl or phenyl(meth)acrylate, multifunctional acrylates and methacrylates such as for example bisphenol-(A)-di(meth)acrylate, bis-GMA (an addition product of methacrylic acid and bisphenol-A-diglycidyl ether), UDMA (an addition product of 2-hydroxyethyl-methacrylate and 2,2,4-hexamethylene diisocyanate), di-, tri- and tetraethylene glycol di(meth)acrylate, decane dioldi(meth)acrylate, trimethylolpropane tri(meth)acrylate, pentaerythritol tetra(meth)acrylate and butanediol di(meth)acrylate, 1,10-decanediol di(meth)acrylate or 1,12-dodecanediol di(meth)acrylate.

The polymerizable monomers are preferably used in a quantity of 1 to 80 weight-%, more preferably 5 to 50 weight-% and most preferably 5 to 30 weight-% relative to the total mass of polymerizable monomer and silane of formulae (I) or precondensed products derived from them.

The mixtures can in addition contain further additives such as colorants (pigments and dyes), stabilizers, aromatic substances, microbiocidal active ingredients, flame-retardants, plasticizers and/or UV-absorbers.

Furthermore, the compositions for improving the mechanical properties can be filled with organic or inorganic particles or fibres. Preferred inorganic particulate fillers are amorphous spherical materials based on mixed oxides of $SiO_2$, $ZrO_2$ and/or $TiO_2$ (DE 40 29 230 A1), microfine fillers such as pyrogenic silicic acid or precipitation silicic acid as well as macrofillers (particle size from 5 μm to 200 μm) or minifillers (particle size from 0.5 to 5 μm) such as quartz, glass ceramic or glass powders, in particular barium and strontium silicate glass powder, lithium-aluminium silicate glass powder, silicon, zirconium and aluminium oxides or their mixed oxides with an average particle size of 0.5 μm to 5 μm as well as X-ray opaque fillers such as ytterbium trifluoride. In addition, glass fibres, polyamide or carbon fibres can also be used as fillers.

The silanes according to the invention can be used as such or in hydrolytically condensed or partially polymerized form as varnishes for coating plastics, glass or other substrates. In addition, they are suitable as adhesives, adhesion promoters and for the preparation of contact lenses, fillers and bulking materials for composites and in particular medical materials such as dental materials.

The methylene dithiepane silanes according to the invention, polysiloxanes derived from them as well as compositions which contain, in addition to the methylene dithiepane silane(s) and/or polysiloxanes, initiator, monomer, additive and/or filler, are particularly suitable as dental materials such as adhesives, coating materials, dental cements and filling materials.

A preferred composition contains:
(a) 5 to 99.9 weight-%, preferably 5 to 90 weight-%, more preferably 10 to 70 weight-% polysiloxane; and
(b) 0.1 to 5.0 weight-%, preferably 0.2 to 2.0 weight-% polymerization initiator; and preferably
(c) 1.0 to 80 weight-%, preferably 5.0 to 50 weight-% ionically and/or radically polymerizable monomer; and preferably
(d) 1.0 to 90 weight-%, preferably 2.0 to 80 weight-% fillers.

The amounts are in each case relative to the total mass of the dental material.

The invention is explained in more detail in the following examples.

EXAMPLE 1

Synthesis of N-[3-(triethoxysilyl)propyl]-[2-(6-methylene-1,4-dithiepane)methyl]carbamate

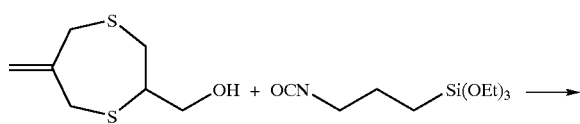

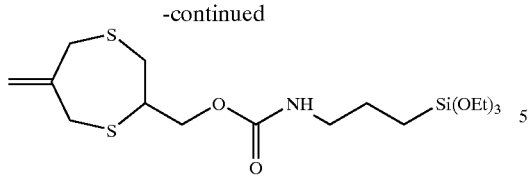

11 g (45 mmol) of 3-isocyanatopropyl triethoxy silane are added dropwise to an ice-cooled solution of 8 g (45 mmol) of 2-hydroxymethyl-6-methylene-1,4-dithiepane which was prepared according to WO 96/19471 and a drop of Metatin 812 (dibutyltin dilaurate) in 15 ml of dried methylene chloride. After 14 hours' stirring at room temperature, the NCO band is no longer detectable at 2280 cm$^{-1}$ in the IR-spectrum, and the solvent is then distilled off at reduced pressure accompanied by the introduction of dry air. 17.6 g (92%) of a pale-coloured liquid with a refractive index of $n_D{}^{25}$=1.5039 remain.

IR (film): 3342 (s), 2973 (s), 2976 (s), 1723 (s), 1634 (w), 1530 (m), 1443 (m), 1393 (m), 1241 (m) and 1078 (s) cm$^{-1}$.

$^1$H-NMR (CDCl$_3$): ä=0.63 (t, 2H, CH$_2$Si), 1.24 (t, 9H, CH$_3$), 1.62 (m, 2H, CH$_2$), 2.91–3.18 (m, 5H, CH$_2$N+CH$_2$S+ CHS), 3.59 (m, 4H, =CCH$_2$S), 3.83 (q, 6H, SiOCH$_2$), 4.26 (m, 2H, CHCH$_2$O), 5.04 (d, 2H, =CH$_2$) and 5.52 (br., 1H, NH) ppm.

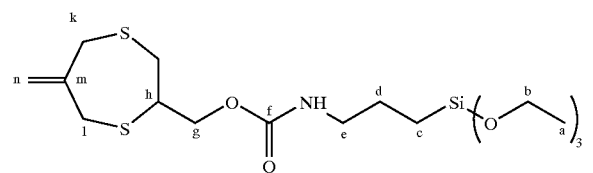

$^{13}$C-NMR (CDCl$_3$): ä=8.0 (c), 18.6 (a), 23.5 (d), 35.5 (i), 39.2 (h), 40.5 (e), 43.8 (l), 49.4 (k), 58.7 (b), 65.7 (g), 111.7 (n), 148.0 (m) and 156.3 (f) ppm.

EXAMPLE 2

Hydrolytic Condensation of N-[3-triethoxysilyl) propyl]-[2-(6-methylene-1,4-diethiepane)methyl] carbamate 100 mmol of the silane are dissolved in 192 ml anhydrous THF. The hydrolysis is carried out by the addition of 3.0 mol water in the form of 0.1 aqueous HCl. After 72 hours, stirring at room temperature (RT), the volatile components are removed in vacuum and a viscous resin forms which shows a degree of condensation of 72% as determined by $^{29}$Si-NMR spectroscopy. The resin formed can be used as a monomer component for radical polymerization.

EXAMPLE 3

Preparation of a Dental Cement Based on the Sol-Gel Component from Example 2

According to Table 1 below, a composite fixing cement was prepared on the basis of A) a methacrylate mixture and B) incorporating the hydrolytic condensate from Example 2 based on N-[3-(triethoxysilyl)propyl]-[2-(6-methylene-1,4-diethiepane)methyl]carbamate by means of an Exakt-type roll mill (Exakt Apparatebau, Norderstedt). Suitable specimens, prepared from the materials, were irradiated twice for 3 minutes with a dental light source (Spectramat, Vivadent) in the wavelength range of 370 to 520 nm.

It is clear from Table 2 that material A with the conventional methacrylate mixture shows the greatest polymerization shrinkage.

TABLE 1

Cement composition

| Substances | Material A Proportions (wt. - %) | Material B Proportions (wt. %) |
|---|---|---|
| urethane dimethylacrylate[1] | 31.6 | 31.6 |
| dodecanediol dimethylacrylate | 7.8 | — |
| hydrolytic condensate from Example 2 | — | 7.8 |
| Aerosil OX-50 (Degussa) | 41.2 | 41.2 |
| ytterbium trifluoride (Rhone-Poulenc) | 18.7 | 18.7 |
| photoinitiator[2] | 0.7 | 0.7 |

[1] urethane dimethacrylate of 2 mol 2-hydroxyethyl methacrylate and 1 mol 2,2,4-trimethylhexamethylene diisocyanate-1,6
[2] 1:1 mixture of camphorquinone and N,N-diethyl-3,5-di-tert.butylaniline

TABLE 2

Cement properties

| Material properties | Material A | Material B |
|---|---|---|
| Polymerization shrinkage (vol. - %) | 4.9 | 2.6 |
| Flexural strength according to ISO 4049 (MPa) | 86 | 54 |
| Flexural-E-modulus according to ISO 4049 (GPa) | 3.19 | 2.86 |

EXAMPLE 4

2-[(3-Triethoxysilylpropyl)aminocarbonyl]-benzoic acid-(6-methylene-1,4-dithiepane-2-yl)methylester Step 1: 6-Methylene-1,4-dithiepanyl-2-yl-methyl Hydrogen Phthalate 5.7 g (56.7 mmol) of triethylamine in 20 ml methylene chloride are added dropwise at room temperature to a solution of 10 g (56.7 mmol) 2-hydroxymethyl-6-methylene-1,4-dithiepane, 8.4 g (56.7 mmol) phthalic anhydride, 100 mg MeHQ and 50 mg DMAP (4-(N,N'-dimethylaminopyridine) in 40 ml methylene chloride. After 20 hours' stirring at 35 to 40° C. accompanied by the introduction of dry air, the reaction mixture is washed 4 times each with 40 ml of 2N HCl and 4 times each with 40 ml water. Drying is carried out over sodium sulphate and the solvent distilled off on a rotary evaporator first at 100 mbar, later in a fine vacuum. 14.3 g (77.7% yield) of an orange liquid remain, which gradually crystallizes out to give a beige solid. Melting point: 78.5–79° C.

IR (KBr pressing): 3345 (w), 3076 (m), 2955 (m), 2899 (m), 1736 (s), 1686 (s), 1424 (m), 1286 (s) and 1121 (m) cm$^{-1}$.

$^1$N-NMR (CDCl$_3$): ä=2.93–3.21 (m, 3H, SCH$_2$/SCH), 3.50–3.69 (m, 4H, SCH$_2$), 4.45–4.83 (m, 2H, OCH$_2$), 4.85 (d, 2H, =CH$_2$), 7.58–7.94 (m, 4H, aromatic H) and 11.0 (br, 1H, COOH) ppm.

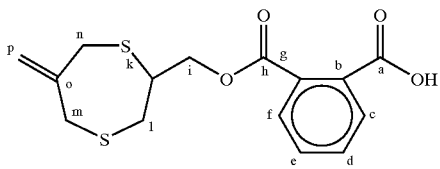

$^{13}$C-NMR (CDCl$_3$); ä=34.6 (l), 37.6 (n), 39.9 (m), 47.5 (k), 66.4 (i), 111.6 (p), 128.7–133.0 (b, c, d, e, f, g), 147.4 (o), 167.6 (h) and 172.2 (a) ppm.

Step 2: 2-[(3-Triethoxysilylpropyl)aminocarbonyl]-benzoic Acid-(6-methylene-1,4-dithiepane-2-yl)methyl Ester 8.5 g (44 mmol) of EDC (N-(3-dimethylaminopropyl)-N'-ethylcarbodiimidohydrochloride) are added portionwise at 0° C. to a solution of 13 g (40 mmol) of 6-methylene-1,4-dithiepanyl-2-methyl hydrogen phthalate, 9 g (40 mmol) of 3-aminopropyl triethoxy silane and 94 mg DMAP. The reaction mixture is stirred for 2 hours at 0° C. and a further 36 hours at room temperature. The course of the reaction is followed using IR spectroscopy. After the methylene chloride has been largely distilled off on the rotary evaporator, the residue is taken up with 150 ml ethyl acetate and washed successively with 150 ml each of ice-cold 0.3 N HCl, with ice-cold 0.3 M sodium carbonate solution and with ice-cold saturated sodium chloride solution. After drying over sodium sulphate, the solvent is removed first at approximately 100 mbar and thereafter in fine vacuum. 9.5 g (45% yield) of a yellow liquid with a refractive index $n_D^{25}$=1.5373 remain.

IR (film): 3464 (w), 2973 (m), 2926 (m), 1773 (s), 1715 (s), 1396 (s) and 1078 (s) cm$^{-1}$.

$^1$H-NMR (CDCl$_3$): ä=0.68 (t, 2H, CH$_2$Si), 1.24 (t, 9H, CH$_3$), 1.78–1.82 (m, 2H, CH$_2$), 2.95–3.20 (m, 3H, CH$_2$S/CHS), 3.28–3.40 (br, 1H, NH), 3.50–3.69 (m, 6H, =C—CH$_2$S)/NHCH$_2$), 3.72–3.85 (m, 8H, CH$_2$O), 4.84 (d, 2H, =CH$_2$) and 7.50–7.85 (m, 4H, aromatic H) ppm.

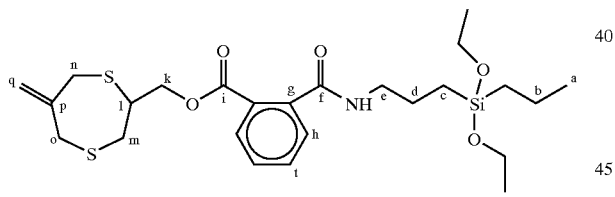

$^{13}$C-NMR (CDCl$_3$): ä=6.6 (c), 17.2 (a), 21.2 (d), 34.0 (m), 37.8 (n), 38.9 (o), 39.3 (e), 51.5 (l), 57.3 (b), 65.4 (k), 110.1 (q), 122.0 (h), 131.0 (g), 133.8 (t), 146.6 (p) and 167.2–167.5 (f, i) ppm.

What is claimed is:

1. A polysiloxane based on one or more methylene dithiepane silanes according to Formula I

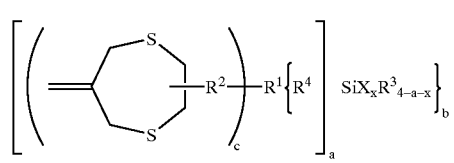

wherein $R^1$=a saturated or unsaturated aliphatic or alicyclic hydrocarbon radical with 1 to 10 carbon atoms which can be interrupted by one or more oxygen and/or sulphur atoms and can contain one or more ester, carbonyl, amide and/or urethane groups, or is an aromatic or heteroaromatic hydrocarbon radical with 6 to 18 carbon atoms;

$R^2$=has one of the meanings given for $R^1$ or is absent;

$R^3$=has one of the meanings given for $R^1$ or is absent;

$R^4$=—(CHR$^6$)$_n$—, —Y—CO—NH—(CHR$^6$)$_n$—, —Y—CO—NH—R$^5$—, —(CHR$^6$)$_n$—S—R$^5$—, —S—R$^5$—, —CO—O—R$^5$ or is absent, with n=1 to 4, R$^6$=hydrogen, C$_1$ to C$_{10}$ alkyl or C$_6$ to C$_{10}$ aryl, R$^5$ has one of the meanings given for R$^1$ and Y stands for an O or S atom or is absent;

X=is a hydrolyzable group;

a, b, c and x each independently of each other are 1, 2 or 3; with the sum of a+x=2 to 4, wherein b is 1 when a is greater than 1 and a is 1 when b is greater than 1; and optionally one or more further hydrolytically condensable compounds.

2. A polysiloxane according to claim 1, wherein $R^1$, $R^2$, and/or $R^3$ is a saturated or unsaturated aliphatic or alicyclic hydrocarbon radical with 1 to 8 carbon atoms, which can be interrupted by oxygen or sulphur atoms, ester, carbonyl, amide and/or urethane groups, or is an aromatic hydrocarbon radical with 6 to 10 carbon atoms;

$R^4$=—(CHR$^6$)$_n$—, —Y—CO—NH—(CHR$^6$)$_n$—, —Y—CO—NH—R$^5$—, —S—R$^5$—, —CO—O—R$^5$— or is absent, with n=1 to 3, R$^6$=hydrogen or C$_1$ to C$_4$ alkyl, R$^5$ has one of the meanings given for R$^1$ and Y stands for an O or S atom or is absent;

X=halogen, hydroxy, C$_1$ to C$_3$ alkoxy or C$_1$ to C$_3$-acyloxy;

a=1;

b=1 or 2;

c=1 or 2; and/or x=2 or 3.

3. A polysiloxane according to claim 1, wherein $R^1$=a saturated or unsaturated aliphatic or alicyclic hydrocarbon radical with 1 to 6 carbon atoms or an aromatic hydrocarbon radical with 6 to 10 carbon atoms;

$R^2$=a saturated or unsaturated aliphatic hydrocarbon radical with 1 to 4 carbon atoms, which can contain an oxygen atom or an ester group, or is absent;

$R^3$=a methyl, ethyl and/or phenyl group or is absent;

$R^4$=—(CH$_2$)$_n$— or —Y—CO—NH—(CH$_2$)n—, with n=1 to 3 and Y stands for an O atom or is absent; and/or X=methoxy, ethoxy or chlorine.

4. A polysiloxane according to claim 1, wherein one or more radicals $R^1$ to $R^6$ are optionally substituted by C$_1$ to C$_{10}$ alkyl groups, C$_6$ to C$_{10}$ aryl groups, halogen, hydroxy, alkoxy, hydroxylalkyl, carboxy, —SO$_3$H, —PO$_3$H$_2$ and/or —PO$_4$H$_2$.

5. A polysiloxane according to claim 1, wherein $R^2$ is substituted in position 2 or 3 of the 1,4-dithiepane ring.

6. A composition containing a polysiloxane according to claim 1.

7. A polysiloxane according to claim 6, wherein the further hydrolytically condensable compound is a compound of silicon, aluminum, zirconium, titanium, boron, tin, vanadium or phosphorus.

8. A polysiloxane according to claim 7, wherein the further hydrolytically condensable compound is a silane according to Formula (VI)

$$R^7{}_k(Z'R^8)_m SiX'_{4-(k+m)} \qquad \text{Formula (VI)}$$

wherein $R^7$ stands for a C$_1$ to C$_8$ alkyl, C$_2$ to C$_{12}$ alkenyl or C$_6$ to C$_{14}$ aryl group;

$R^8$ stands for a $C_1$ to $C_8$ alkylene, $C_2$ to $C_{12}$ alkenylene or $C_6$ to $C_{14}$ arylene group;

X' stands for a hydrogen or halogen atom or a $C_1$ to $C_8$ alkoxy group;

Z' stands for a glycidyl, acryl, methacryl, vinyl, allyl or vinyl ether group;

k is equal to 0, 1, 2 or 3;

m is equal to 0, 1, 2 or 3; and k+m is equal to 0, 1, 2 or 3;

a zirconium, titanium compound of Formula (VII)

$$MeX''_y R^9_z \qquad \text{Formula (VII)}$$

wherein

Me stands for Zr or Ti;

$R^9$ stands for a hydrogen atom, a substituted or unsubstituted $C_1$ to $C_{12}$ alkyl, $C_1$ to $C_{15}$ alkylaryl or $C_6$ to $C_{14}$ aryl group;

X" stands for a halogen atom, a hydroxyl or $C_1$ to $C_8$ alkoxy group;

y is equal to 1 to 4; and z is equal to 1 to 3;

an aluminium compound according to Formula (VIII)

$$Al\, R^{10}_3 \qquad \text{Formula (VIII)}$$

wherein $R^{10}$ stands for a halogen atom, a hydroxyl or $C_1$ to $C_8$ alkoxy group;

and/or is a boron trihalide, tin tetrahalide, tin tetraalkoxide and/or a vanadyl compound.

9. A polysiloxane according to claim 8, wherein $R^7$=a $C_1$ to $C_3$ alkyl, $C_2$ to $C_5$ alkenyl or a phenyl group;

$R^8$=a $C_1$ to $C_5$ alkylene, $C_2$ to $C_5$ alkenylene or a phenylene group;

X'=a halogen atom, a methoxy or ethoxy group;

Z'=an acryl or methacryl group;

k=0 and 1;

m=0 and 1;

k+m=0, 1 or 2; and/or $R^9$=is a $C_1$ to $C_5$ alkyl or a phenyl group;

X"=is a halogen atom, a methoxy, ethoxy or propoxy group;

y=4;

z=0 or 1; and/or $R^{10}$=a halogen atom or a $C_1$ to $C_5$ alkoxy group.

10. A polysiloxane according to claim 8, containing 1 to 90 mol-% of one or more silanes according to the general Formula (VI) or precondensed products derived from them; and/or 0 to 70 mol-% of one or more zirconium and/or titanium compounds of the general Formula (VII) or precondensed products derived from them; and/or 0 to 70 mol-% of one or more aluminum compounds of the general Formula (VIII) or precondensed products derived from them, relative to the total mass of compounds of Formula (I) and/or precondensed products derived from them and compounds of Formula (VI), Formula (VII) or (VIII).

11. A polysiloxane according to claim 6, containing 10 to 99 mol-% of a silane according to Formula (I) relative to the monomeric starting compounds.

12. A composition according to claim 6, further comprising an ionically and/or radically polymerizable monomer.

13. A composition according to claim 12, further comprising a methyl, ethyl, butyl, benzyl, furfuryl, and/or phenyl (meth)acrylate, bisphenol-A-di(meth)acrylate, the addition product of methacrylic acid and bisphenol-A-diglycidylether the addition product of 2-hydroxyethyl-methacrylate and 2,2,4-hexamethylene diisocyanate, di-, tri-, or tetraethylene glycol di(meth)acrylate, decanediol methacrylate, trimethylol propane tri(meth)acrylate, pentaerythritol tetra(meth)acrylate, butanediol di(meth)acrylate, 1, 10-decanediol dio(meth)acrylate or 1, 12-dodecanediol di(meth)acrylate or a mixture of these monomers.

14. A composition according to claim 6, further comprising a filler.

15. A composition according to claim 6, further comprising an initiator for radical polymerization.

16. A composition according to claim 6, further comprising (a) 5 to 99.9 weight-% polysiloxane; and (b) 0.1 to 5.0 weight-% polymerization initiator; and optionally (c) 1.0 to 80 weight-% ionically and/or radically polymerizable monomer;

(d) 1.0 to 90 weight-% filler.

17. A dental material comprising a composition according to claim 6.

18. A dental composite material comprising a composition according to claim 6.

19. A dental cement comprising a composition according to claim 6.

20. A dental filling material comprising a composition according to claim 6.

21. A dental bonding material comprising a composition according to claim 6.

* * * * *